United States Patent [19]
de la Parra

[11] Patent Number: 4,782,077

[45] Date of Patent: Nov. 1, 1988

[54] TALISCANIN AND OTHER ARISTOLACTAMS FOR TREATING NEUROLOGICAL DISORDERS, PARKINSON'S DISEASE, ALZHEIMER DISEASE AND IMPOTENCE

[75] Inventor: Jacinto J. de la Parra, Mexico City, Mexico

[73] Assignee: Monoclonetics International, Inc., Houston, Tex.

[21] Appl. No.: 87,432

[22] Filed: Aug. 20, 1987

[51] Int. Cl.$^4$ ............................................ A61K 31/40
[52] U.S. Cl. ..................................................... 514/423
[58] Field of Search ......................................... 514/423

[56] References Cited

PUBLICATIONS

"The Aristolochic Acids and Aristolactams", *Journal of Natural Products*, vol. 5, No. 5 (1982), by D. B. Mix et al.

"Tumor Inhibitors x. Photochemical Synthesis of Phenanthrenes Synthesis of Aristolochic Acid and Related Compounds", Journal of Organic Chemistry, vol. 30, by S. M. Kupchan and H. C. Warmser.

"The Aristolochic Acids and Aristolactams," *Isoquinoline Alkaloid Research*, Plenum Press, Chapter 17 (1978), by Channer.

Nervous System, "A Strategic Approach to Parkinson's", *Emergency Medicine*, 95-11 (Apr. 30, 1987), by J. Fermaglich.

Las Aristoloquias Medicinales, *Anales de el Instituto Medico Nacional Mexicod*, Mexico D. F., Tomo VIII, 16.

"La Taliscanina, un Componente De Aristolochia Taliscana", *Cincia Mexico*, vol. 24, by L. Maldanado et al.

Primary Examiner—Stanley J. Friedman
Attorney, Agent, or Firm—Eric P. Mirabel

[57] ABSTRACT

A method of treating neurological disorders, in particular Parkinson's disease, is disclosed. The method involves administering an aristolactam, especially Taliscanin, an extract of the root of Aristolochia Taliscana, to an afflicted patient. The dosage is varied in accordance with the patient's response, and generally ranges from 300 to 4000 micrograms per day. Taliscanin has also been shown effective in treating Alzheimer disease and impotence.

14 Claims, No Drawings

TALISCANIN AND OTHER ARISTOLACTAMS FOR TREATING NEUROLOGICAL DISORDERS, PARKINSON'S DISEASE, ALZHEIMER DISEASE AND IMPOTENCE

FIELD OF THE INVENTION

The invention relates to the use of Taliscanin, and other aristolactams, in the treatment of neurological disorders, Parkinson's disease, Alzheimer disease, and impotence.

BACKGROUND OF THE INVENTION

Among neurological disorders, Parkinson's disease is one of the most common. In the United States alone, there are over one million patients who suffer from it. In addition, the number of Parkinson patients is constantly increasing. The increase is because the disease is an illness of the middle and late years of life, and people are today living longer. Further, the patients with the disease tend to live on for many years, hence, their numbers accumulate.

Parkinson's disease most frequently begins between the ages of forty and seventy, with a peak age of onset being in the sixth decade. It is estimated that about one percent of the population over the age of fifty is afflicted.

The characteristic symptoms of Parkinson's disease include movement problems, such as impedance of alternating movements, bradykinesia (slowness of movement), akinesia, or hypokinesia, a tremor (which occurs at rest but not usually during volunatry movement), stooped posture, rigidity, and an expressionless face.

The onset of the disease is characterized by a reduction in the rate of blinking, relative immobility and poverty of movement, and the characteristic tremor. As the disease develops the poverty of movement becomes more apparent, and is shown by infrequency of swallowing, slowness of chewing, disinclination to adjust the position of the body and limbs, and the lack of movements of cooperation, for example, arising from a chair without first adjusting the feet.

Patients frequently exhibit a festinating gait—losing balance and "chasing" the center of gravity to avoid losing balance. Rigidity (alternating or continuous firming and tensing of the muscles), usually also appears. Eventually, due to tensing of the frontal muscles, the patient takes on a stooped posture. Similarly, tensing of the flexor muscles in the hands and feet can cause a permanent bent attitude of these extremities.

Potentially the most serious problem for the patient is dementia, which is commonly associated with Parkinson's disease. In one study it was reported that the incidence of dementia in Parkinson's disease patients was ten times as high as for their age matched spouses. Parkinson's patients with dementia have been reported to become more seriously involved in a shorter period of time and to respond less well to standard L-dopa therapy.

Parkinson's disease can be of three separate types: the post-encephalitic, idiopathic, and the arteriosclerotic type. The post-encephalitic type is not true Parkinson's disease inasmuch as it is not degenerative. It stems from an infection that involves not only the basal ganglia but the entire nervous system. The infection was caused by a virus which appeared during the worldwide influenza epidemics of 1917 to 1927.

The arteriosclerotic type, contrary to what was earlier believed, is now thought to be the same as the idiopathic ('unknown cause") type. The same symptoms occur, except that they are accompanied by arteriosclerosis. The arteriosclerotic type usually occurs in older people and involves more severe symptoms than the more common idiopathic type.

Physiologically speaking, Parkinsonism is a disease of the extrapyramidal motor system. This system governs automatic, static, postural, and other motor activities of the nervous system which are not readily modifiable. On the anatomical level, however, Parkinsonism is a progressive disease of the basal ganglia, i.e., the small center or nucleus at the base of the brain.

The extrapyramidal motor system is believed to be controlled by the basal ganglia and certain other brainstem nuclei. The striatum and the substantia nigra are both component structures of the basal ganglia. Parkinsonism is believed to be caused by aberrations in the neurotransmitters in the striatum and the substantia nigra, which in turn cause degeneration of neurons in those areas.

Neurotransmitters are substances which are synthesized and stored in the presynaptic terminals. A synapse is a functional junction between two neurons, where a nerve impulse is transmitted from one neuron to another. In response to an appropriate stimulus, a neurotransmitter is released across the synaptic gap to combine with specific receptor sites on the postsynaptic neuron.

The most important neurotransmitters from the point of view of basal ganglionic function are acetylcholine, dopamine, gamma aminobutyric acid (GABA), and serotonin. Acetylcholine exists at high concentrations in the striatum. It is synthesized and released by the small (Golgi type 2) neostriatal neurons, upon which it has an excitatory effect.

Dopamine is one of the family of neurotransmitters known as catecholamines, the others in that family being epinephrine, and norepinephrine. Dopamine is a precursor in the synthesis of epinephrine, which in turn is a precursor for norepinephrine. The areas of the brain which are richest in dopamine are the substantia nigra and the striatum, where it is localized in synaptic endings of nigral fibers. Stimulation of the substantia nigra causes a release of dopamine, which has an inhibitory effect on the neostriatal neurons.

Normally, the extrapyramidal system functions properly due to the interaction between two antagonistic systems. One of these systems is to some extent regulated by serotonin and the catecholamines, and the other by acetylcholine and histamine. The interaction between these two antagonistic systems is known as the balance between the wakeful and sleep states, or the circadian cycle.

In Parkinson's disease the levels of the catecholamines are reduced. In particular, concentrations of dopamine are greatly decreased in the striatum and the substantia nigra. This may result either because the synthesis of dopamine is blocked, or because the enzymes which metabolize it (monoamine oxidase) are increased.

The decreased release of dopamine in the striatum which occurs in Parkinson's disease disinhibits the neurons that synthesize acetylcholine. This causes a predominance of cholinergic (acetylcholine-like) activity.

The most notable aspect of the pathology of Parkinson's disease is that there is a loss of pigmented cells in the substantia nigra and other pigmented nucleii. The normal ranges for nigral cells is about 425,000 for a young adult diminishing to about 200,000 at age eighty. In most Parkinson's patients there are less than 100,000. The degree of dopamine deficiency in the substantia nigra correlates with the degree of cell loss in this area.

Inasmuch as cholinergic activity predominates in Parkinsonism, one method of treatment is to administer anticholinergic drugs to restore the ratio between dopamine and acetylcholine. Typical anticholinergic drugs are belladonna and trihexylphenidyl. A related method of treatment involves administration of dopaminergic agents, e.g., L-dopa, amantadine, and bromocriptine. This causes an increase in the otherwise reduced levels of dopamine.

The problem with anticholinergic substances is that they cause a variety of undesirable side effects, including myocardium infarction, glaucoma, toxic psychosis, anxiety, hallucinations, nausea, vomiting, urine retention in protatitics, prostatic hypertrophy, constipation, miosis (contraction of the pupil), intraocular hypertension, mouth dryness, dyschezias, and orthostatic hypotension. Dopaminergic agents cause other side effects, such as the induction of involuntary movements including restlessness, grimacing, choreoathetosis and dystonia of the limbs, neck, and trunk.

It is clear, therefore, that a drug which has less severe side effects than the dopaminergic and anticholinergic agents currently in use would be of great benefit in the treatment of Parkinsonism.

It is also suspected that other neurological disorders of the extrapyramidal system are caused by the same mechanism, and the same areas of the brain are affected, as in Parkinsonism. A number of other disorders can cause some or all of the symptoms of Parkinson's disease. For example, Alzheimer disease can cause elements of parkinsonian akinesia, rigidity, poor balance, and tremor. A drug which treats Parkinsonism should, therefore, also be useful in treatment of such neurological disorders.

The compound Taliscanin has, until now, been used in treating snake bites. It has never been used or suggested for use in treating neurological disorders, Alzheimer disease, or impotency.

SUMMARY OF THE INVENTION

It has been discovered that Taliscanin, an extract from the root of Aristolochia Taliscana, alleviates the symptoms of Parkinsonism and related neurological disorders. Taliscanin has also been found effective in the treatment of Alzheimer disease and impotency. Taliscanin should also be effective in treating paralysis which is secondary to cerebral vascular accidents or strokes, diabetes insipidus, choreasyvenhims, obesity secondary to hypothalmic disorders and amenorrohea secondary to hypothalmic disorders, deafness of neurological origin and mutism.

Taliscanin has far fewer side effects than encountered with the conventional Parkinson's treatments such as dopaminergic and anticholinergic agents. Further, it is believed to actually regenerate at least some of the damaged or injured neurons of the substantia nigra, i.e., those which are not in the latter stages and, thus, may be effective in reducing aging and increasing longevity.

Taliscanin has the following chemical formula:

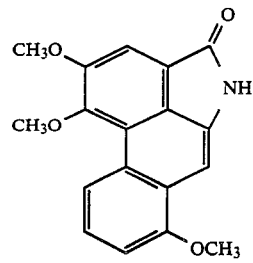

Taliscanin is one of the family known as aristolactams, which family has the following generic formula:

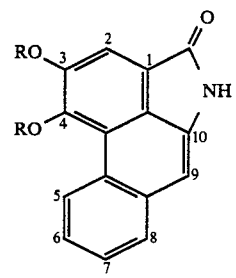

It is believed that several aristolactam derivatives may have the same therapeutic activity as does Taliscanan. Among these are the aristolams shown in Channer, "The Aristolochic Acids and Aristolactams," Isoquinoline Alkaloid Research, Plenum Press, Chapter 17 (1978), for example, aristolactam, aristored, aristolochic acid-D methyl ether lactam, aristolactam Beta-D-glucoside, aristolactam-A11, aristolactam-A111, aristolactam-B11 (cepharanone-B), aristolactam-B111, cepharanone-A, and doryflavine.

DESCRIPTION OF THE PREFERRED EMBODIMENTS

Taliscanin, and the aristolactams, are well-known compounds which are described in D. B. Mix et al. "The Aristolochic Acids and aristolactams," Journal of Natural Products, Vol. 45 No. 5 (1982). Taliscanin can be extracted from the root of Aristolochia Taliscana. The extraction process is well-known in the art, and is described in L. Maldanado et al., "La Taliscanina, un Componente de Aristolochia Taliscana" Cincia Mexico Vol. 24 at p. 237 (1966); Channer, "The Aristolochic Acids and Aristolactams," Isoquinoline Alkaloid Research, Plenum Press, Chapter 17 (1978). It should also be possible to synthesize Taliscanin, although that has not yet been done.

For the sake of completeness, one example of an extraction process follows.

EXAMPLE 1

Extraction Process 9.1 kg of the root of Aristolochia Taliscana was pulverized and then suspended in undiluted hexane. The suspension was then acted on by a Soxhlet extractor until all the hexane was exhausted. The residue was then suspended in benzene, which was again exhausted by a Soxhlet extractor. 143.0 grams of the resulting brown residue was then dissolved in a 2:3 mixture of benzene-hexane, and the solution was fractionated through an alumina chromatography column. Polar fractions were then eluted with a 7:3 benzene-ether mixture.

This procedure yields 13.8 grams of Taliscanin, having a melting point of 272°–273° C., maxima UV absorption of 242, 254, 310, 395 millimicrons; E of 38900, 35490, and 16220. It showed infra red absorption at 3450 cm$^{-1}$ (CHCH$_3$), and 1690 cm$^{-1}$ (NH) (carbenito of lactam) and a 1615 cm$^{-1}$ aromatic double bond.

EXAMPLE 2

Preparation of Medication

Clinical trials were conducted with Taliscanin to test its efficacy in treating Parkinsonism and other neurological disorders. The Taliscanin was prepared for oral administration to the patients by the following method.

100 ml of 96 proof ethanol was mixed with a sufficient amount of distilled water to bring the final alcohol solution to 60 proof. 20 mg of Taliscanin were added, and the solution was shaken.

Another batch was made up for particularly sensitive patients, the only difference being that in this solution the final alcohol concentration was 30 proof.

The alcohol/water solutions prepared were protected from sunlight by storage in amber glass. Storage can be at room temperature or under refrigerated conditions.

It should be emphasized that an alcohol/water solution is only one example of a suitable vehicle for Taliscanin. Other possible vehicles are distilled water, lactose, and dextrose/water, e.g., Dextrose Water 5.

EXAMPLE 3

Administration of the Medication

The Taliscanin in solution was administered to the patients in the clinical trial at the rate of 300 mg of Taliscanin (three drops of solution) per day. The patients were checked once per week, or less often if weekly check-ups were too inconvenient.

The check-up involved monitoring the patient's rigidity, marche, facie, tremor, and supination pronation (forearm movement) for improvement. The degree of dilation of the pupils is an important parameter in the evaluation of the patient, and this was also monitored to determine whether it was normalizing. It was also determined whether the patient suffered from insomnia, which is a side effect of the drug where the dosage is too large. The only other known side effect is a painful erection in some males.

Patients that showed an improvement were kept on the same dosage of Taliscanin. For those that did not, the dosage was increased to 600 micrograms (six drops) per day, and they were followed up two weeks later. For any which still showed no improvement, the dosage was increased another three drops per day until there was an improvement or until the maximum dose was reached.

The maximum clinical dose was arrived at following a toxicity study on dogs. This study showed a lethal dose of Taliscanin to be 4.0 mg for a 35 kg dog. Based on this result, it was estimated that 8.0 mg would kill a 70 kg man. The maximum clinical dose administered was reduced considerably from the 8.0 gram level, It was, in fact, only 4.0 mg per day.

The medication is taken orally every one to six hours as required to administer the daily dosage. To prevent insomnia in patients receiving a total of 900 micrograms per day or more, the medication should not be given later than two hours before bedtime.

It is recommended that 1 ml per week of Hyaluronidase (Wydase T.M.) be administered intramuscularly for the first four to six months of treatment. Hyaluronidase increases the permeability to Taliscanin of the blood/brain barrier and of the pre and postsynaptic terminals. However, Hyaluronidase is contraindicated for patients who are pregnant or who tend to bleed, for example, due to hemophilia.

Other agents which increase the permeability of the blood/brain barrier and/or the pre and postsynaptic terminals, for example Papavaina (available in Mexico), can be substituted for Hyaluronidase.

Once the symptoms of Parkinsonism, e.g., tremor and impaired motion, are no longer apparent the treatment can be stopped. To withdraw from medication, the dosage is gradually tapered off in increments of three drops per week. Gradual withdrawal is recommended because a sudden cessation of medication can, in some instances, cause relapse. Although relapse is not a common problem, caution nevertheless suggests a gradual withdrawal.

An alternative to complete cessation of medication is placing the patient on a maintenance dosage. This course is recommended where symptoms reappear as the dosage is decreased. The maintenance dosage is usually from 50 to 100 micrograms per day.

As mentioned above, Taliscanin was also effective in treating impotence and Alzheimer disease. The normal dosage for the treatment of impotence is 300 to 900 micrograms per day, and for Alzheimer Disease, it is 300 to 1200 micrograms per day.

It is emphasized that the medication can be administered by a number of methods other than orally, e.g., intravenously or intramuscularly. It can also be given at a variety of dosages. The parameters listed above are merely those that were used in these clinical trials.

Clinical Results

Taliscanin was administered to several thousand patients with various neurological disorders and Parkinsonism symptoms, using the above-described protocol. The results of the treatment, as broken down by patients showing predominant symptoms, appear in Table I below. Of these patients, approximately one-third of those in the first two (early) stages of Parkinson's disease were completely cured. Patients in the third and fourth (late) stages of the disease were not cured but were, in most cases, improved by Taliscanin.

Taliscanin was also effective in curing and improving various other neurological disorders related to and/or causing the same symptoms as Parkinsonism. See Table II below.

TABLE 1

EXTRAPYRAMIDAL SYSTEM SYMPTOMS (CLINICAL CASES) INDICATING DESCENDING NERVE TRACTS THAT DO NOT ENTER INTO THE FORMATION OF THE PYRAMIDS OF THE MEDULLA

| Symptoms | Total | Cure | Moderate Improvement | Without Improvement | Success* Rate |
|---|---|---|---|---|---|
| HYPERKINESIA (rapid movements) | 2,236 | 652 | 1,390 | 194 | 91.32% |
| AKINESIA (low motility) | 2,603 | 923 | 1,532 | 148 | 94.31% |
| HYPERTONIA (excess tension of muscles or arteries) | 1,415 | 625 | 706 | 84 | 94.06% |
| HYPOTONIA (reduced tension) | 375 | 54 | 248 | 73 | 80.53% |
| AUTONOMIC DYSFUNCTION (dysfunction of independent organs) | 157 | 70 | 71 | 16 | 90.00% |
| RESTING TREMOR - SYNDROME OF PARKINSON (trembling in a static pose) | 378 | 168 | 192 | 18 | 95.24% |
| INTENTION OR ACTION TREMOR AND TREMOR WITH A LESION IN THE CEREBELLUM (tremor in a moving state; active, static) | 173 | 39 | 108 | 26 | 85.00% |
| CHOREA-ATHETOSIS (spasmodic movement of facial and extremity muscles) CHOREA, HEMIBALLISM, DYSTONIA, ATHETOSIS (involuntary movements on one side of the body; state of hyper-tonicity or hypotonicity) | 44 | 21 | 22 | 1 | 97.73% |
| PROPULSION MARCHE (walking too fast and falling) | 142 | 90 | 43 | 9 | 93.66% |
| OPTOKINETIC INSTAGMUS (eye twitching) | 36 | 8 | 22 | 6 | 83.33% |
| DYSSYNERGIA (loss of power of muscular coordination) | 504 | 166 | 306 | 32 | 93.65% |

*Number of patients cured together with those showing moderate improvement as a percentage of the total.

TABLE II

TREATMENT WITH TALISCANIN OF PARKINSON'S DISEASE AND RELATED NEUROLOGICAL DISORDERS

| Etiology | Total | Cure | Moderate Improvement | Mild Improvement | Without Improvement |
|---|---|---|---|---|---|
| VIRAL INFECTIONS: | | | | | |
| *Encephalitis lethargica* (viral) | 596 | 229 | 244 | 56 | 67 |
| Influenza | 633 | 299 | 209 | 65 | 60 |
| SYPHILIS | 105 | 24 | 44 | 18 | 19 |
| TUBERCULOSIS | 766 | 270 | 300 | 100 | 96 |
| VICERAL MYCOSIS (fungal) | 146 | 33 | 43 | 23 | 47 |
| CYSTICERCOSIS (parasitic) | 54 | 38 | 37 | 8 | 9 |
| EXOGENOUS INTOXICATION BY CARBON MONOXIDE | 50 | in majority of patients | 5 | 4 | 3 |
| EXOGENOUS INTOXICATION BY MANGANESE | 45 | — | 23 | 9 | 13 |
| COLLATERAL EFFECTS OF DRUGS: | | | | | |
| Antipsychotics: | | | | | |
| (a) Largactil | 324 | 48 | 140 | 78 | 58 |
| (b) Sinogan | 32 | 7 | 6 | 15 | 4 |
| (c) Piportil | 88 | 32 | 33 | 11 | 12 |
| (d) Haldol | 90 | 28 | 35 | 15 | 12 |
| Blood Pressure | | | | | |
| (a) Reserpina | 436 | 121 | 172 | 54 | 89 |
| HEAD TRAUMA | 59 | 29 | 13 | 7 | 10 |
| CEREBRALVASCULAR SCLEROSIS | 375 | 165 | 149 | 38 | 23 |
| ATHEROSCLEROSIS (Parkinson's Disease) | 89 | 32 | 36 | 18 | 3 |
| IDIOPATHIC PARKINSON'S DISEASE | 2,155 | 497 | 767 | 439 | 452 |
| SYNDROMES: | | | | | |
| (a) Von Monakov (viral) | 61 | 36 | 11 | 4 | 10 |
| (b) Delhermitte van Bogaert | 130 | 48 | 44 | 12 | 26 |
| (c) De Parinaud | 31 | 12 | 13 | 5 | 1 |

It can be seen that Taliscanin was effective in curing or improving the vast majority of patients with Parkinsonian symptoms, Parkinson's disease, and other neurological disorders. Because of the similarity in structural formula, it is believed that other aristolactams will also be effective in treating these disorders.

It should be understood that all descriptions herein are exemplary only and that the scope of the protection is defined in the claims which follow.

What is claimed is:

1. A method of treating neurological disorders or impotence comprising administering an effective amount of an aristolactam to an afflicted patient.

2. The method of claim 1 wherein the aristolactam is Taliscanin.

3. The method of claim 2 wherein the neurological disorder is Parkinson's disease, Alzheimer disease, or a disorder which causes some of the symptoms of Parkinson's disease.

4. The method of claim 3 wherein the dosage of Taliscanin administered is from 300 to 4000 micrograms per day.

5. The method of claim 3 wherein the dosage of Taliscanin administered is 300 micrograms per day.

6. The method of claim 3 wherein the Taliscanin is administered in a solution consisting essentially of ethanol and Taliscanin.

7. The method of claim 6 wherein the alcohol concentration of the final solution is between 30 and 60 proof.

8. The method any of claims 2 to 7 further including administering Hyaluronidase to the treated patient.

9. A method of treating Parkinson's disease and neurological disorders causing parkinsonian symptoms comprising:
administering 300 micrograms per day of Taliscanin to an afflicted patient;
increasing the dosage of Taliscanin to 600 micrograms per day if the patient does not improve.

10. The method of claim 9 wherein the Taliscanin is administered in a solution which includes one or more members selected from the group consisting of ethanol, lactose, dextrose, and water.

11. The method of claim 10 wherein the alcohol concentration of the final solution is between 30 and 60 proof.

12. The method of any of claims 9 to 11 further including administering an agent which increases the permeability to Taliscanin of the blood/brain barrier and of the pre and postsynaptic terminals selected from the group consisting of Hyaluronidase and Papavaina.

13. A method for treating Parkinson's disease comprising:
administering 300 to 4000 mg per day of Taliscanin to an affected patient.

14. The method of claim 9 further including, for a patient who does not improve on administering 600 micrograms per day, increasing the dosage of Taliscanin in increments of 300 micrograms per day until the patient improves or to a maximum of 4,000 micrograms per day.

* * * * *

UNITED STATES PATENT AND TRADEMARK OFFICE
CERTIFICATE OF CORRECTION

PATENT NO. : 4,782,077
DATED : November 1, 1988
INVENTOR(S) : Jacinto Juarez de la Parra It is certified that error appears in the above—identified patent and that said Letters Patent is hereby corrected as shown below:

Column 5, line 40: change "mg" to -- micrograms --.

Column 6, line 2: change "gram" to -- mg --.

Signed and Sealed this

Twentieth Day of June, 1989

Attest:

DONALD J. QUIGG

Attesting Officer      Commissioner of Patents and Trademarks